United States Patent
Wismans et al.

(10) Patent No.: US 11,419,279 B2
(45) Date of Patent: Aug. 23, 2022

(54) AIRBORNE ROOTING AND CALLUSING OF CUTTINGS

(71) Applicant: Dümmen Group B.V., De Lier (NL)

(72) Inventors: Perry Th. J. G. Wismans, De Lier (NL); J. F. J. M. van den Heuvel, Rotterdam (NL)

(73) Assignee: Dümmen Group B.V., De Lier (NL)

(*) Notice: Subject to any disclaimer, the term of this patent is extended or adjusted under 35 U.S.C. 154(b) by 0 days.

(21) Appl. No.: 16/963,538

(22) PCT Filed: Jan. 21, 2019

(86) PCT No.: PCT/IB2019/050495
§ 371 (c)(1),
(2) Date: Jul. 21, 2020

(87) PCT Pub. No.: WO2019/142166
PCT Pub. Date: Jul. 25, 2019

(65) Prior Publication Data
US 2021/0045303 A1    Feb. 18, 2021

Related U.S. Application Data

(60) Provisional application No. 62/673,314, filed on May 18, 2018, provisional application No. 62/630,419, filed on Feb. 14, 2018, provisional application No. 62/620,206, filed on Jan. 22, 2018.

(51) Int. Cl.
*A01G 31/02* (2006.01)
*A01H 4/00* (2006.01)
*A01N 3/00* (2006.01)

(52) U.S. Cl.
CPC .......... *A01G 31/02* (2013.01); *A01H 4/008* (2013.01); *A01N 3/00* (2013.01)

(58) Field of Classification Search
CPC .................................................. A01G 31/02
See application file for complete search history.

(56) References Cited

U.S. PATENT DOCUMENTS

| | | | |
|---|---|---|---|
| 2,431,890 | A | 12/1947 | Raines |
| 4,514,930 | A | 5/1985 | Schorr et al. |
| 4,976,064 | A | 12/1990 | Julien |
| 6,601,342 | B2 | 8/2003 | Dümmen |
| 7,082,718 | B2 | 8/2006 | Dümmen |
| 2012/0137580 | A1 | 6/2012 | Dekker |

FOREIGN PATENT DOCUMENTS

| | | |
|---|---|---|
| DE | 19844020 C2 | 12/2000 |
| DE | 10211723 C1 | 7/2003 |
| WO | 2016189021 A1 | 12/2016 |

OTHER PUBLICATIONS https://fiestafarms.ca/12372/garden/calluses-are-a-good-thing-when-rooting-houseplants (Retrieved from the Internet Apr. 20, 2021).*
"Fiesta Farms Blog" Dec. 16, 2014, https://fiestafarms.ca/12372/garden/calluses-are-a-good-thing-when-rooting-houseplants (retrieved from the Internet on Apr. 2021). (4 pages total).*
"A Piece of Rainbow, Grow African Violets from Leaf Cuttings," Jan. 21, 2016, https://www.apieceofrainbow.com/grow-african-violet/ (retrieved from the Internet on Apr. 20, 2021). (14 pages total).*
https://gardenpool.org/online-classes/how-to-make-a-simple-5-gallon-bucket-aeroponics-system (Retrieved from the Internet on Mar. 31, 2022).*
https://www.nasa.gov/vision/earth/technologies/aeroponic_plants.html (Retrieved from the Internet on Mar. 31, 2022).*
Santos et al., "Stem Versus Foliar Uptake During Propagation of Petunia xhybrida Vegetative Cuttings", HortScience, 2009, pp. 1974-1977, vol. 44(7).

* cited by examiner

*Primary Examiner* — Susan McCormick Ewoldt
(74) *Attorney, Agent, or Firm* — The Webb Law Firm

(57) ABSTRACT

Provided herein are devices, systems, and methods for airborne rooting and/or callusing of cuttings. The device includes a container defining an interior that can be humidified to allow for development of calluses or roots.

2 Claims, 12 Drawing Sheets

AIRBORNE ROOTING AND CALLUSING OF CUTTINGS

CROSS-REFERENCE TO RELATED APPLICATIONS

This application is the United States national phase of International Application No. PCT/IB2019/050495 filed Jan. 21, 2019 and claims priority to U.S. Provisional Patent Application Nos. 62/620,206 filed Jan. 22, 2018, 62/630,419 filed Feb. 14, 2018, and 62/673,314 filed May 18, 2018, the disclosures of which are hereby incorporated by reference in their entirety.

BACKGROUND OF THE INVENTION

Field of the Invention

Provided herein are devices, systems, and methods for generating calluses and/or roots on unrooted cuttings.

In particular, provided herein are devices, systems, and methods for airborne generation of roots on unrooted cuttings, without the need for or use of a growth medium.

Description of Related Art

In the flowering ornamental plant industry, commercial plant products are typically generated through asexual reproductions of a particular plant or plants having desirable traits. These asexual reproductions take the form of cuttings.

Because the flowering ornamental plant industry is an international market, many breeders and growers are outside of the United States. However, U.S. Department of Agriculture regulations limit the importation of plants. In particular, plants cannot be imported in soil. Thus, imported flowering ornamentals are typically unrooted cuttings.

These unrooted cuttings are imported, planted in a growth medium to allow root formation and then are transplanted to a final receptacle for commercial sale. This extra step, allowing for root growth prior to commercial sale, is time consuming, requires additional space that could be used for other horticultural purposes, is costly, and the extra handling of cuttings increases the risk of damage or loss of product.

While hydroponics is known, the process can be costly and time consuming, and hydroponic methods can increase susceptibility to and transmission of pathogens. Accordingly, the need exists in the field to develop methods that allow for cost-effective, large-scale rooting of cuttings

SUMMARY OF THE INVENTION

Provided herein is a device for airborne rooting and/or callusing of cuttings including a container comprising a top surface and sidewalls defining an interior; at least one opening in the top surface or a sidewall, the at least one opening configured to allow optional humidification of the interior; and at least one opening, optionally an elongated opening, in the top surface, the at least one opening configured to receive a receptacle holding one or more unrooted cuttings such that one or more roots develop in the interior.

Also provided herein is a system for airborne rooting and/or callusing of cuttings including a device as described herein: a humidity sensor; optionally a humidifier; and at least one computer in communication with the humidity sensor and the optional humidifier.

Also provided herein is a method for airborne rooting and/or callusing of cuttings including the steps of inserting at least one receptacle holding at least one unrooted cutting in the elongated opening of a device as described herein: humidifying the interior to generate rooted cuttings and removing the receptacle holding the rooted cuttings from the elongated opening.

Also provided herein is a method for airborne rooting and/or callusing of cuttings including the steps of providing at least one receptacle holding at least one unrooted cutting and humidifying the unrooted cutting to generate at least one callused or rooted cutting.

Also provided herein is a method of planting rooted cuttings, including the steps of receiving a strip of receptacles holding one or more rooted cuttings, wherein the cuttings have been rooted as described herein, separating a receptacle holding a rooted cutting from the strip of receptacles, and planting the receptacle holding the rooted cutting in a growth medium.

Also provided herein is a kit including at least one strip having a plurality of receptacles, each receptacle configured to hold one or more unrooted cuttings, and at least one support configured to hold the at least one strip and allow humidification of the one or more unrooted cuttings.

Further embodiments or aspects are set forth in the following numbered clauses:

Clause 1: A device for airborne rooting and/or callusing of cuttings comprising a container comprising a top surface and sidewalls defining an interior; at least one opening in the top surface or a sidewall, the at least one opening configured to optionally allow humidification of the interior; and at least one elongated opening in the top surface, the at least one elongated opening configured to receive a receptacle holding one or more unrooted cuttings such that one or more calluses or roots develop in the interior.

Clause 2: The device according to clause 1, wherein the container further comprises a bottom surface, and wherein the top surface, sidewalls, and bottom surface define the interior Clause 3: The device according to clause 1 or clause 2, wherein the interior is sealed, optionally airtight from atmosphere.

Clause 4: The device according to any of clauses 1-3, wherein the container is liquid impermeable.

Clause 5: The device according to any of clauses 1-4, wherein the container is vapor impermeable.

Clause 6: The device according to any of clauses 1-5, wherein the at least one opening comprises at least two openings.

Clause 7: The device according to clause 6, wherein at least one of the at least two openings is configured to hold a humidity sensor within the interior.

Clause 8: The device according to clause 7, further comprising a humidity sensor disposed in the interior.

Clause 9: The device according to any of clauses 1-8, further comprising a mechanism to humidify the interior.

Clause 10: The device according to clause 9, wherein the mechanism is a humidifier, a fogging device, a vaporizer, a nebulizer, an ultrasonic humidifier, an impeller humidifier, an evaporative humidifier, or any other device configured to increase humidity within the interior.

Clause 11: The device according to any of clauses 1-10, wherein the at least one elongated opening comprises at least two elongated openings.

Clause 12: The device according to any of clauses 1-11, wherein the at least one elongated opening is configured to receive a strip comprising a plurality of receptacles, each receptacle holding one or more unrooted cuttings, optionally wherein the receptacle is formed of a biodegradable material, optionally wherein the biodegradable material comprises at least one nutrient, growth promoter, growth regulator, components to control pests and diseases, and/or antibiotic, such that as the biodegradable material degrades, the at least one nutrient, growth promoter, growth regulator, and/or antibiotic is released from the strip.

Clause 13: The device according to any of clauses 1-12, wherein the container is at least partially opaque.

Clause 14: The device according to any of clauses 1-13, wherein the container is formed of or coated with a material that substantially prevents transmission of light therethrough, optionally wherein the interior is maintained at or below 10.8 lux.

Clause 15: A system for airborne rooting and/or callusing of cuttings comprising the device of any of clauses 1-14; a humidity sensor; optionally a humidifier; and at least one computer in communication with the humidity sensor and the optional humidifier.

Clause 16: The system of clause 15, wherein the computer is programmed or configured to receive humidity data from the humidity sensor, compare the humidity data to a predetermined humidity level, and control the humidifier to increase or decrease humidity in the interior based on the comparison.

Clause 17: The system of clause 16, wherein the predetermined humidity level is stored on a database.

Clause 18: The system of clause 17, wherein the database stores a range of suitable humidity levels for each of a plurality of varieties of cuttings.

Clause 19: The system of any of clauses 15-18, further comprising a source of water for the humidifier, and wherein the source of water comprises at least one nutrient, growth promoter, microbial control agent, pest and/or disease control agent, and/or growth regulator.

Clause 20: A method for airborne rooting and/or callusing of cuttings, comprising inserting at least one receptacle holding at least one unrooted cutting in the elongated opening of the device of any of clauses 1-14; humidifying the interior to generate callused or rooted cuttings; and removing the receptacle holding the callused or rooted cuttings from the elongated opening.

Clause 21: The method of clause 20, wherein the interior is kept at or below 10.8 lux.

Clause 22: The method of clause 20 or clause 21, wherein the interior is kept at below 1.08 lux.

Clause 23: The method of any of clauses 20-22, wherein the interior is kept at below 0.0108 lux.

Clause 24: The method of any of clauses 20-23, wherein the callused or rooted cuttings are contacted with a nutrient solution and/or coated and packaged for shipment.

Clause 25: The method of clause 24, wherein the callused or rooted cuttings are coated with a polymeric solution or suspension comprising one or more of sodium alginate, agar, polyacrylamide, agarose, biodegradable plastics, and gelatin.

Clause 26: The method of clause 25, wherein the polymeric solution or suspension comprises at least one nutrient, growth promoter, growth regulator, microbial control agent, pest and/or disease control agent and/or antibiotic.

Clause 27: A method for airborne rooting and/or callusing of cuttings, comprising providing at least one receptacle holding at least one unrooted cutting; and humidifying the unrooted cutting to generate at least one callused or rooted cutting.

Clause 28: The method of clause 27, wherein the at least one receptacle is held within a support structure configured to place the at least one unrooted cutting in proximity to, but not in direct contact with, water or other source of humidity.

Clause 29: The method of clause 28, wherein the at least one receptacle is held in a container configured to hold standing water or other source of humidity and/or to allow a flow of water or other source of humidity therethrough.

Clause 30: The method of any of clauses 27-29, wherein the at least one unrooted cutting is watered from above, optionally where the at least one unrooted cutting is never watered from below.

Clause 31: The method of clause 27, wherein a basal portion of the at least one unrooted cutting is kept at below 10.8 lux.

Clause 32: The method of clause 27, wherein the receptacle is formed of a biodegradable material.

Clause 33: The method of clause 32, wherein the biodegradable material comprises at least one nutrient, growth promoter, growth regulator, and/or antibiotic, such that as the biodegradable material degrades, the at least one nutrient, growth promoter, growth regulator, components to control pests or diseases, and/or antibiotic is released.

Clause 34: The method of any of clauses 27-33, wherein the callused or rooted cuttings are contacted with a nutrient solution and/or coated and packaged for shipment.

Clause 35: The method of clause 34, wherein the callused or rooted cuttings are coated with a polymeric solution or suspension comprising one or more of sodium alginate, agar, polyacrylamide, agarose, biodegradable plastics, and gelatin.

Clause 36: The method of clause 35, wherein the polymeric solution or suspension comprises at least one nutrient, growth promoter, growth regulator, microbial control agents, pest and/or disease control agent, and/or antibiotic.

Clause 37: A method of planting rooted cuttings, comprising receiving a strip of receptacles holding one or more rooted cuttings, wherein the cuttings have been rooted according to the method of any of clauses 20-36; separating a receptacle holding a rooted cutting from the strip of receptacles; and planting the receptacle holding the rooted cutting in a growth medium.

Clause 38: The method of clause 37, wherein the growth medium is soil.

Clause 39: A kit comprising: at least one strip comprising a plurality of receptacles, each receptacle configured to hold one or more unrooted cuttings; and at least one support configured to hold the at least one strip and allow humidification of the one or more unrooted cuttings.

Clause 40: The kit of clause 39, wherein the at least one support comprises an opaque barrier configured to hold a basal end of an unrooted cutting in relative darkness, optionally at 10.8 lux or less.

DESCRIPTION OF THE INVENTION

Figure 1:
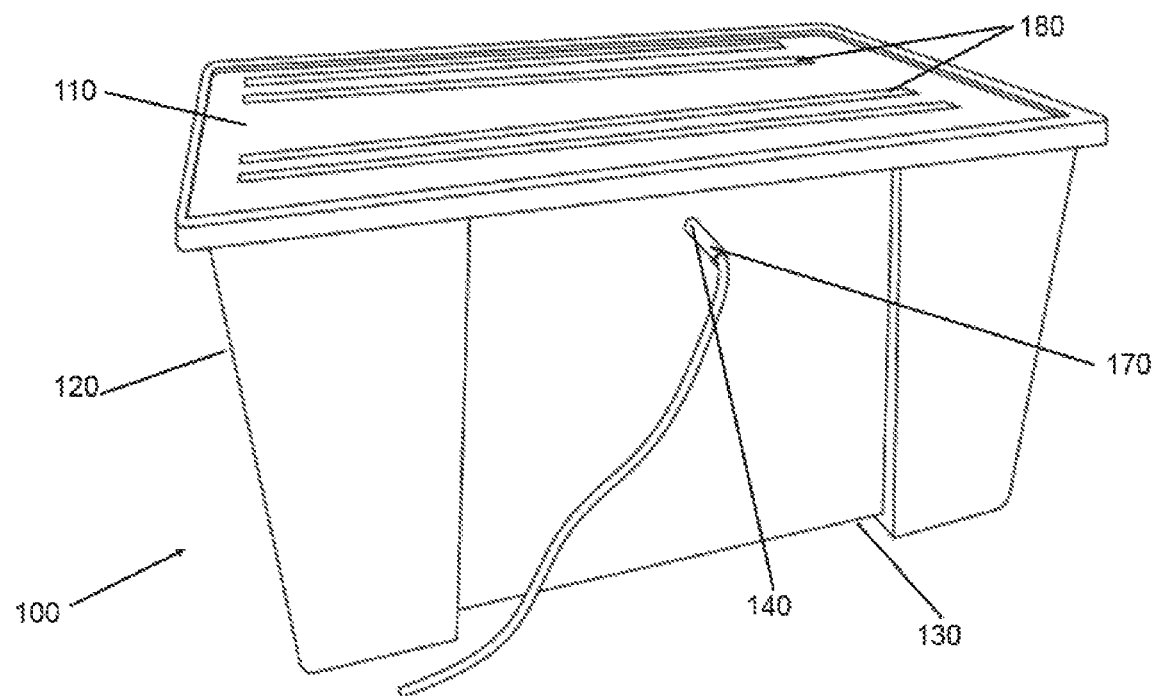
FIG. 1 is a perspective view of a device according to a non-limiting embodiment or aspect of the present invention.
Figure 2:
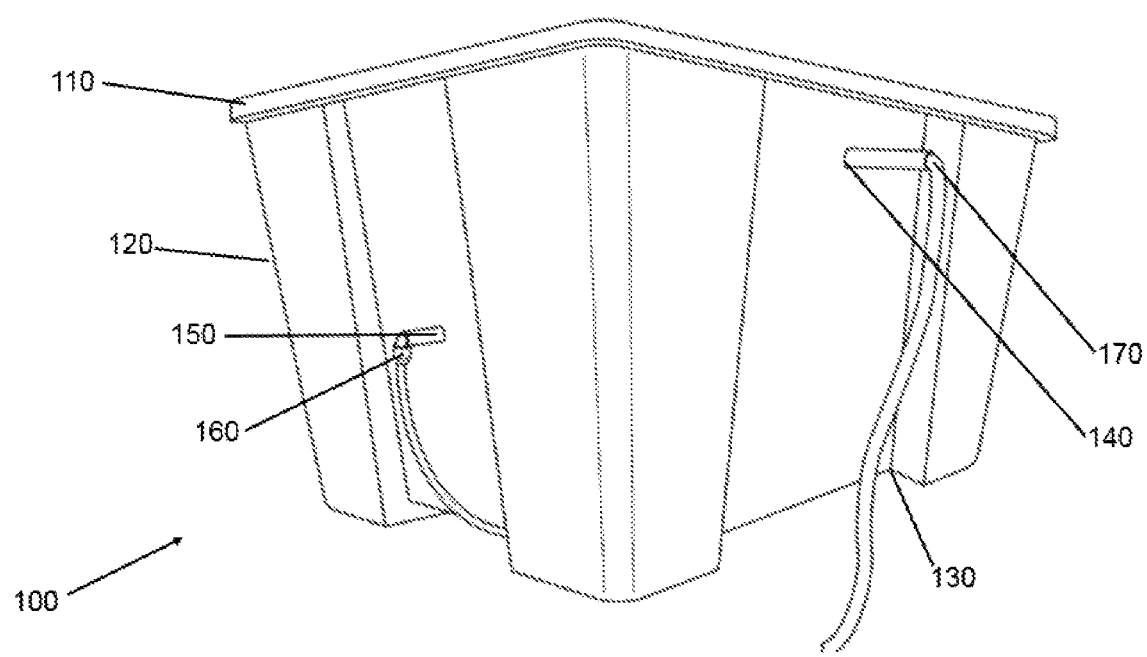
FIG. 2 is a perspective view of a device according to a non-limiting embodiment or aspect of the present invention.
Figure 3:
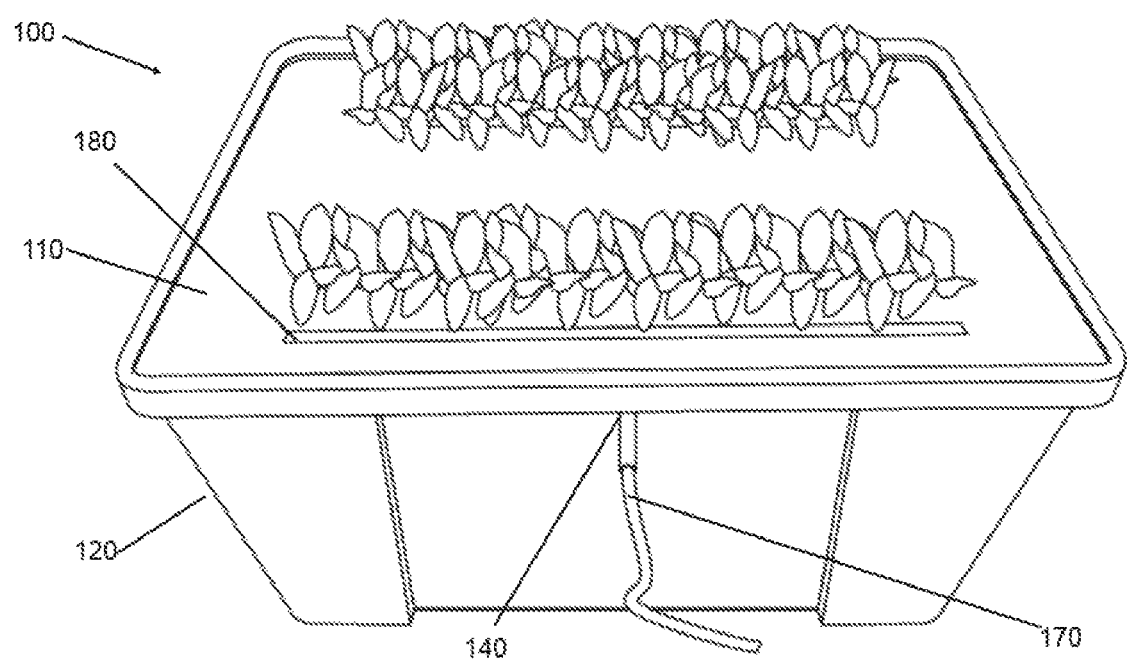
FIG. 3 is a perspective view of a device according to a non-limiting embodiment or aspect of the present invention.
Figure 4:
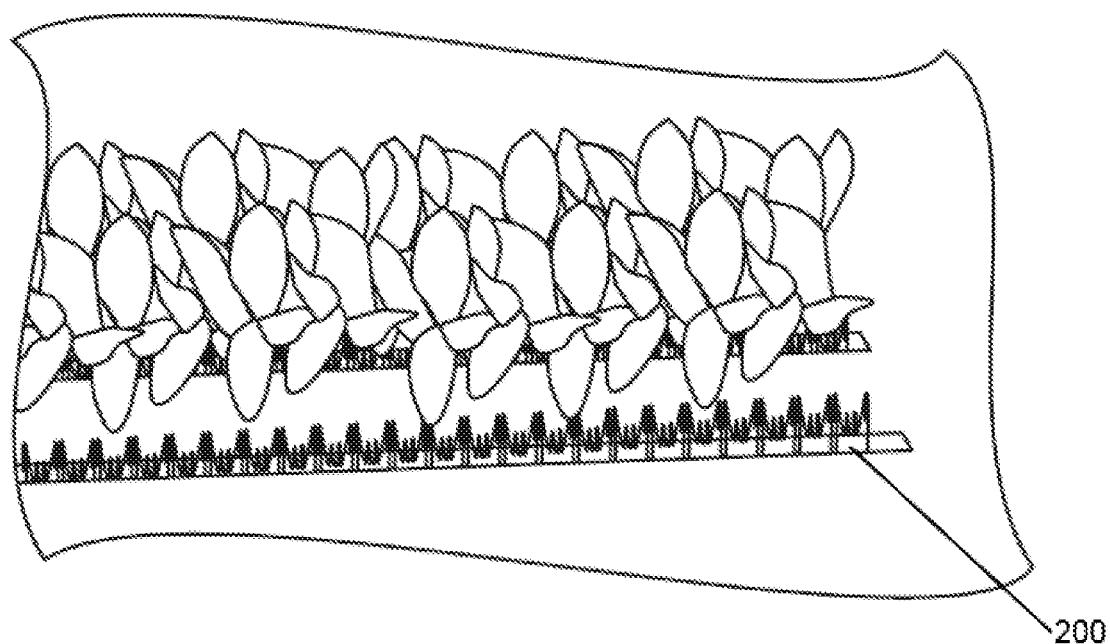
FIG. 4 is a close-up view of a device according to any of FIGS. 1-3.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

All references cited within this specification are incorporated by reference herein in their entirety.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention can assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The figures accompanying this application are representative in nature, and should not be construed as implying any particular scale or directionality, unless otherwise indicated.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

Provided herein is a device, a system, and a method for airborne rooting and/or callusing of cuttings. As used herein, the term "airborne rooting" excludes hydroponics and methods that involve immersion of a cutting or part thereof in a liquid. In some non-limiting aspects or embodiments, "airborne rooting" means no direct application of a liquid to the basal portion of an unrooted cutting. As used herein, the term "cutting" refers to any plant part from which roots may emanate/develop, such as leaves, stolons, runners, eyes from tubers, scales from bulbs, in vitro plant material, and the like.

As used herein, any reference to rooting of cuttings will refer to development of calluses as well. As used herein, callus or calluses refers to a growing mass of unorganized plant parenchymal cells. Parenchymal cells cover a plant wound, for example, an area where a cut is made to produce a plant cutting.

While the following description provides a number of embodiments or aspects for the airborne rooting of cuttings, it should be understood that a commonality is maintaining the cutting in an environment with high relative humidity, in embodiments or aspects 70%, 75%, 80%, 85%, 90%, 95%, or higher relative humidity (all subranges therebetween inclusive), without direct immersion of the cutting in a liquid (e.g., without hydroponic methods), and, in some non-limiting embodiments or aspects, without any direct application of a liquid to the basal portion of the unrooted cutting. In addition, a commonality across all embodiments or aspects is maintaining the basal portion of the unrooted cutting in a sufficiently low amount of light (i.e., darkness) to ensure basal portion development into roots, such as below 10.8 lux, which is the level of illumination during a typical twilight period of the day. In further non-limiting embodiments or aspects, the interior is kept at below 1.08 lux, at below 0.108 lux, or below 0.0108 lux, all subranges therebetween inclusive.

In an initial step, unrooted cuttings are obtained via known methods. Thereafter, the unrooted cuttings can optionally be cooled to arrest physiological processes interfering with root development and/or stored for a set period of time (e.g., 1, 2, 3, 4, 5, 6, or 7) nights in a cold environment (e.g., 12° C.). In embodiments or aspects in which the unrooted cuttings are rooted in a strip of receptacles, as discussed below, this storage can occur with the unrooted cuttings already placed into the receptacles, such that the strips can then quickly be taken from the cold environment to the rooting environment.

In some non-limiting embodiments or aspects, one or more growth regulators and/or nutrient solutions is applied to the basal portion of the unrooted cuttings prior to initiation of the rooting procedure. In non-limiting embodiments or aspects the one or more growth regulators and/or nutrient solutions includes indole-3-butyric acid (IBA). In non-limiting embodiments or aspects, the concentration of the one or more growth regulators and/or nutrient solutions is from 300-2000 ppm (all subranges therebetween inclusive, and dependent on variety).

As noted above, unrooted cuttings can be placed into a strip of receptacles to allow for rooting of a high volume of cuttings at once. While a strip useful for the present methods can take any useful configuration, including any useful number of receptacles, and can include commercially available strips from known manufacturers, in some non-limiting embodiments or aspects, a strip can include 34-51 receptacles, all subranges therebetween inclusive. In some non-limiting embodiments or aspects, the receptacles include pointed and/or rounded retaining extensions to allow the cutting to be held snugly, and, optionally, removably, within the receptacle. Those of skill in the art will appreciate that the receptacles, including optional retaining elements, can be configured to be useful for species based on species stem thickness, hardiness, vigor, and other known characteristics.

With reference to the accompanying figures, in non-limiting embodiments or aspects, a device for carrying out the present methods can include device (100), which as shown in FIGS. 1-5, can be a container and can include a top surface (110) and sidewalls (120) defining an interior. In some non-limiting embodiments or aspects, the interior of device (100) is airtight, such that humidity provided therein cannot escape, and a generally consistent level of humidity can be maintained. The device (100) may be formed out of any suitable material. In non-limiting embodiments or aspects, the device (100) is formed out of a material that substantially or completely prevents passage of light therethrough. In non-limiting embodiments or aspects, the device (100) is formed of any suitable material and is coated with a material or coating that substantially or completely prevents passage of light therethrough. In non-limiting embodiments or aspects, the illumination level of the interior is 10.8 lux or below, as described previously.

In non-limiting embodiments or aspects, the device (100) further includes a bottom surface (130), such that the interior is surrounded on all sides. In non-limiting embodiments or aspects, the interior of the device (100) is sealed. In further non-limiting embodiments or aspects, the interior of the device (100) is liquid impermeable and/or vapor impermeable.

Figure 5:
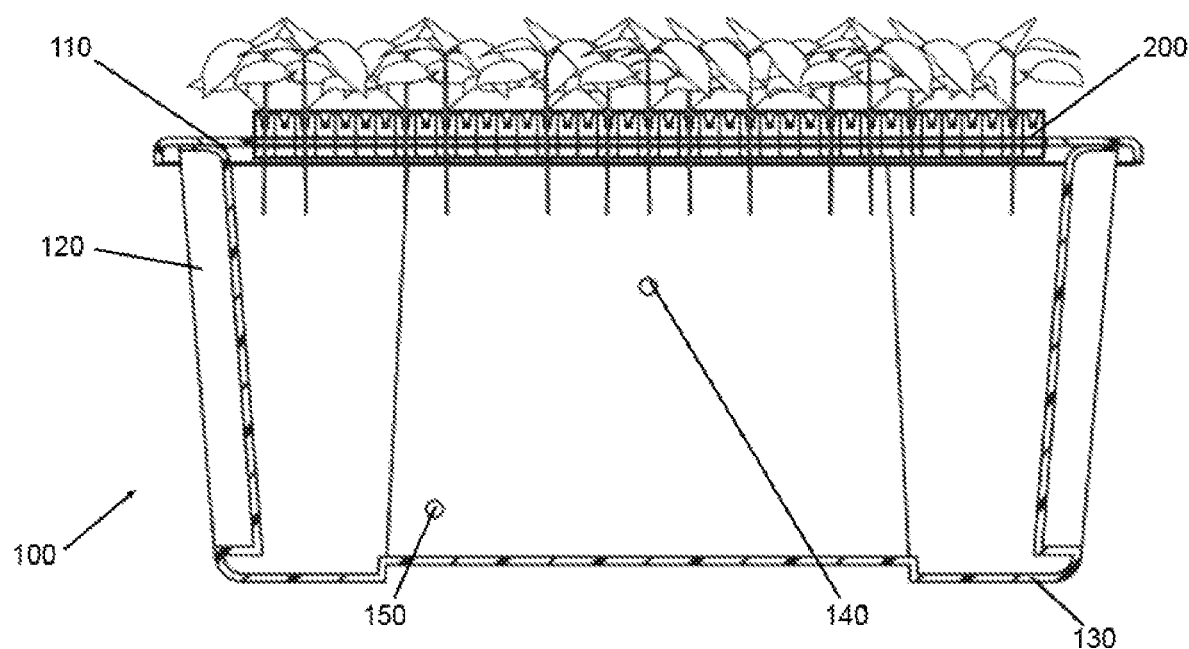
FIG. 5 is a schematic of a cross-sectional front view of a device according to a non-limiting embodiment or aspect of the present invention.

With further reference to the accompanying figures, the device (100) further includes at least one opening (140) in a top surface (110) or sidewall (120) thereof configured to allow humidification of the interior (shown in FIG. 5). In some non-limiting embodiments or aspects, standing water or a porous material loaded with water or the like is placed in the interior and, because the interior can optionally be airtight from the environment, high relative humidity can be maintained in the interior. In some non-limiting embodiments or aspects, the device (100) further includes a second opening (150) in a top surface (110) or sidewall (120) thereof configured to hold a humidity sensor (160) within the interior. As will be discussed below with regard to systems of the present invention, a system for airborne rooting of cuttings includes a humidifier (170) and a humidity sensor (160) configured to be placed in or pass through the openings in the top surface (110) or sidewall (120) of the device (100). Further, while the accompanying figures show a plurality of openings in the device (100) for receiving a humidifier and a humidity sensor, it should be appreciated that a humidifier and/or a humidity sensor could extend through an open bottom or a bottom surface of the device (100).

The device (100) further includes at least one elongated opening (180) configured to receive a receptacle (200) capable of or configured to hold one or more unrooted cuttings therein in a manner such that the cutting stem is disposed in the interior. The elongated opening (180) is configured to cooperate with such a receptacle (200) to place one or more unrooted cuttings in communication with the interior, such that the humid and, optionally dark, interior allows for root formation by the cutting(s) therein. Any number of elongated openings (180) may be provided in the top surface (110) of the device (100).

In certain non-limiting embodiments or aspects, the elongated opening (180) is configured to receive a strip of receptacles (200), as described previously. Each receptacle can hold one or more unrooted cuttings. Such strips are known commercially and in the art, for example, as disclosed in U.S. Pat. Nos. 6,601,342 and 7,082,718, the disclosures of which are incorporated herein by reference in their entirety.

The receptacle or strip of receptacles (200) can be supported in one or more elongated openings (180) of the top surface (110) of the device (100) in a manner that allows the basal portion of the unrooted cutting to be kept in (relative) darkness in the interior of the device, substantially keeping light (natural or artificial) from penetrating to the basal portion of the unrooted cutting, while allowing humidification in the interior. The receptacle or strip of receptacles (200) can be releasably or reversibly received in the elongated openings (180) in any suitable manner, for example and without limitation by sliding a receptacle or strip of receptacles into elongated opening (180), or by friction fit, interference fit, snap fit, or press fit, so long as the basal portion of the unrooted cutting held in the receptacle is shielded from substantially all ambient light (for example, and without limitation, by device (100)) and is capable of being exposed to a humid environment. For example, and without limitation, a receptacle or strip of receptacles (200) may include a shoulder that interacts with and rests on top surface (110), allowing the receptacle to be pressed into elongated opening (180) such that the basal portion of the unrooted cutting passes through the elongated opening (180), thus residing below top surface (110) and in the interior of device (100) in relative darkness.

Figure 7:
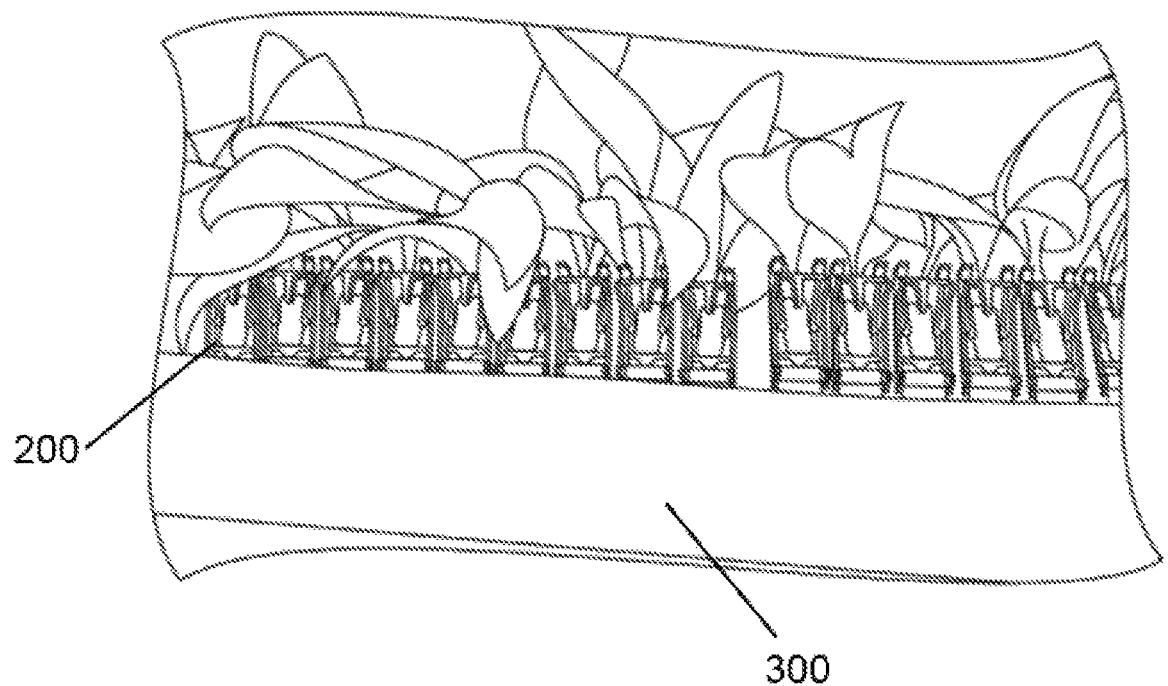
FIG. 7 is a perspective view of a non-limiting embodiment or aspect of the present invention.

In non-limiting embodiments or aspects, the receptacle or strip of receptacles (200) has one or more open sides (e.g., as shown in FIG. 7), allowing open-air rooting, and allowing the basal portion of the unrooted cutting to be humidified in a greater number of ways. For example, a closed-cell receptacle would be limited in terms of the ways in which moisture could be delivered to the basal portion of the cutting. However, with an open-cell/open air rooting design, humidity can be provided in any number of ways, as described herein. In other non-limiting embodiments or aspects, the receptacle or strip of receptacles (200) is formed of a biodegradable material, such that after the cutting(s) develop roots or calluses, the receptacle can be planted, with the cutting therein, in growing medium, and the receptacle can degrade over time. In this way waste can be eliminated. In non-limiting embodiments or aspects, the biodegradable material is formed of, includes, or is impregnated with one or more nutrients, growth promoters, components to control pests or diseases, antibiotics, and/or growth regulators. In this way, as the receptacle degrades, the one or more nutrients, growth promoters, components to control pests or diseases, antibiotics, and/or growth regulators can be released to the roots or calluses of the cutting.

With continuing reference to the accompanying figures, also provided herein is a system for airborne rooting of cuttings. A system includes a device as described herein: a humidifier; and a humidity sensor. Humidity sensors, both digital and analog, are known and are commercially available from, for example and without limitation, Sensirion AG (Staefa, Switzerland), Minco Products, Inc. (Minneapolis, Minn.), and Honeywell (Morristown, N.J.). Humidifiers are also known to those of skill in the art and include, without limitation, fogger/fogging devices, nebulizers, vaporizers, ultrasonic humidifiers, impeller humidifiers, and evaporative humidifiers. It will be appreciated that any type of humidifier can be used, so long as the humidity within the interior can be controlled.

In non-limiting embodiments or aspects, the humidifier and humidity sensor are in communication with a computer. A computer, or computing system, capable of being used with the system described herein may include, but is not limited to, at least one computer having certain components for appropriate operation, execution of code, and creation and communication of data. For example, the computer includes a processing unit (typically referred to as a central processing unit or CPU) that serves to execute computer-based instructions received in the appropriate data form and format. Further, this processing unit may be in the form of multiple processors executing code in series, in parallel, or in any other manner for appropriate implementation of the computer-based instructions.

The computer further includes a system memory with computer storage media in the form of volatile and non-volatile memory, such as ROM and RAM. A basic input/output system (BIOS), with appropriate computer-based routines, assists in transferring information between components within the computer and is normally stored in ROM. The RAM portion of the system memory typically contains data and program modules that are immediately accessible to or presently being operated on by a processing unit, e.g., an operating system, application programming interfaces, application programs, program modules, program data, and other instruction-based computer-readable codes.

A user may enter commands, information, and data into the computer through certain attachable or operable input devices, such as a keyboard, a mouse, etc., via a user input interface. Of course, a variety of such input devices may be utilized, e.g., a microphone, a trackball, a joystick, a touchpad, a touch-screen, a scanner, etc., including any arrangement that facilitates the input of data and information to the computer from an outside source. As discussed, these and other input devices are often connected to the processing unit through the user input interface coupled to the system bus, but may be connected by other interface and bus structures, such as a parallel port, game port, or a universal serial bus (USB). Still further, data and information can be presented or provided to a user in an intelligible form or format through certain output devices, such as a monitor (to visually display this information and data in electronic form), a printer (to physically display this information and data in print form), a speaker (to audibly present this information and data in audible form), etc. All of these devices are in communication with the computer through an output interface coupled to a system bus. It is envisioned that any such peripheral output devices may be used to provide information and data to the user.

The computer may operate in a network environment through the use of a communications device, which is integral to the computer or remote therefrom. This communications device is operable by and in communication with the other components of the computer through a communications interface. Using such an arrangement, the computer may connect with or otherwise communicate with one or more remote computers, such as a remote computer, which may be a personal computer, a server, a router, a network personal computer, a peer device, or other common network nodes, and typically includes many or all of the components described above in connection with the computer. Using appropriate communication devices, e.g., a modem, a network interface or adapter, etc., the computer may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers may be used.

As used herein, the computer includes or is operable to execute appropriate custom-designed or conventional software to perform and implement the processing steps of the method and system of the present invention, thereby forming a specialized and particular computing system. Accordingly, the system and method described herein may include one or more computers or similar computing devices having a computer-readable storage medium capable of storing computer-readable program code or instructions that causes the processing unit to execute, configure, or otherwise implement the methods, processes, and transformational data manipulations discussed hereinafter in connection with the present invention. Still further, the computer may be in the form of a personal computer, a personal digital assistant, a portable computer, a laptop, a palmtop, a mobile device, wearable technology such as a smart watch or other smart accessory, a mobile telephone, a server, or any other type of computing device having the necessary processing hardware to appropriately process data to effectively implement the system and method described herein.

With further reference to the system illustrated in the accompanying figures, in non-limiting embodiments or aspects, the computer may be in wired or wireless connection with the humidifier and the humidity sensor. In non-limiting embodiments or aspects, the computer is programmed or configured to receive humidity data from the humidity sensor and adjusts humidity through control of the humidifier based thereon. In non-limiting embodiments or aspects, the computer is programmed or configured to receive humidity data from a humidity sensor, compare the humidity data to a predetermined humidity value stored in memory or a database, and, based on the comparison, increase or decrease the humidity within the interior. In non-limiting embodiments or aspects, the memory or database stores a range of suitable humidity levels for a plurality of varieties of cuttings.

In further non-limiting embodiments or aspects, in addition to water (or other suitable fluid for providing moisture/humidity to the cutting(s)), the humidifier provides one or more nutrients, growth promoters, microbial control agents, pest and/or disease control agents, antibiotics, and/or growth regulators to the cutting(s). Suitable nutrients, growth promoters, antibiotics, and/or growth regulators for a variety of cuttings are known to those of skill in the art and include compositions including, for example, and without limitation, minerals, trace elements, sugars, amino acids, natural and synthetic auxins, gibberellins and other hormones, and cytokinins and other phytohormones. Such compositions are available commercially.

The one or more nutrients, microbial control agents, pest and/or disease control agents, growth promoters, antibiotics, and/or growth regulators can be provided in a known concentration in a fluid source of a known volume and, in addition to a database or memory storing a range of suitable humidity levels, a range of suitable levels of the one or more nutrients, growth promoters, antibiotics, and/or growth regulators can also be stored, and the humidity sensor and/or the humidifier can communicate an amount of fluid left in a reservoir holding the fluid and one or more nutrients, growth promoters, antibiotics, and/or growth regulators. In this way, the computer system further can control the amount of one or more nutrients, growth promoters, antibiotics, and/or growth regulators provided to the cutting.

In some non-limiting embodiments or aspects, the humidifier can have two or more reservoirs, one containing a known volume of a fluid including the one or more nutrients, growth promoters, antibiotics, and/or growth regulators and one that lacks the one or more nutrients, growth promoters, antibiotics, and/or growth regulators, such that humidity can be continued to be provided at suitable levels, while the levels of the one or more nutrients, growth promoters, antibiotics, and/or growth regulators can be maintained independently.

With continuing reference to the accompanying figures, also provided herein is a method for airborne rooting of cuttings. The method includes the steps of providing one or more unrooted cuttings in a receptacle, or a strip of receptacles, and humidifying the unrooted cuttings to develop roots or calluses. The receptacle, or strip of receptacles, can be placed in an environment, such as a room or compartment, which can be humidified. In other non-limiting embodiments or aspects, the receptacle or strip of receptacles is placed in a humid environment that does not require artificial humidification. In some non-limiting embodiments or aspects, the basal portion of the unrooted cutting is placed in a humid environment wherein, at least in part, humidity is provided by a source of standing water that does not come into contact with the basal portion of the unrooted cutting. In some non-limiting embodiments or aspects, the cuttings are exposed to an illuminance level of 20-25 klux, while the basal portion of the unrooted cuttings (the portion where the cut was made) are kept in low light conditions (i.e., darkness), for example at or below 10.8 lux, which is the level of illumination during a typical twilight period of the day. In further non-limiting embodiments or aspects, the interior is kept at or below 1.08 lux, at or below 0.108 lux, or at or below 0.0108 lux, all subranges therebetween inclusive. In non-limiting embodiments or aspects, for example in embodiments or aspects where high-volume rooting is occurring, cuttings can be maintained on a support surface (as described below, in particular with reference to FIGS. 8-10) that is kept under a cover, for example a plastic roof, and optionally including one or more layers of shading and/or filtering to reduce the impact of direct sunlight on the cuttings. Without wishing to be bound thereby, in one theory the cuttings must be maintained at an illuminance level below 25 klux, for example less than 25, less than 20, or 15 klux or lower, to protect the cuttings.

As noted above, in some non-limiting embodiments of the method, the cuttings are kept in a humid environment including standing water, where the basal portion of the cutting does not contact the water. In other non-limiting embodiments or aspects, the cuttings are watered (e.g., by misting) one or more times per day, for example, and without limitation, 1, 2, 3, 4, 5, 6, 7, 8, 9, or 10 times per day, and the treatment can last for 1, 2, 3, 4, or 5 minutes. In non-limiting embodiments or aspects, watering/misting can occur every twenty minutes. In non-limiting embodiments or aspects, the treatment includes only water. In non-limiting embodiments or aspects, the water includes one or more nutrients, growth regulators, growth promoters, or other like compositions. In non-limiting embodiments or aspects, the water includes electrolytes (e.g., sodium, potassium, and/or phosphate) and has a pH of between 5 and 6.5, optionally between 5.5 and 6, all subranges therebetween inclusive. In non-limiting embodiments or aspects, the water includes one or more of $Ca_2NO_3$, $NH_4$, $NO_4$, $KNO_3$, $HNO_4$, Mn, Zn, $(NH_4)_2SO_4$, $KPO_4$, $KNO_3$, $MgNO_3$, $MGSO_4$, $H_2PO_4$, Cu, NaMo, B, and/or a water-soluble iron chelate. In non-limiting embodiments, the watering/misting occurs from above the cuttings. In non-limiting embodiments or aspects, watering/misting never occurs from below the cuttings (e.g., no direct application of any liquid to the basal portion of the cutting). In further non-limiting embodiments or aspects, the water, optionally including nutrients, growth regulators, growth promoters, or the like, pools in an area underneath the cuttings, and can be maintained there to maintain humidity between waterings. In non-limiting embodiments or aspects, the watering/misting occurs from below the cuttings.

In some non-limiting embodiments or aspects, unrooted cuttings are pinched one or more times during the rooting process. As used herein, the term "pinching" means that apical meristems are removed.

In further non-limiting embodiments or aspects, after the cuttings have rooted or callused, the cutting is treated with a nutrient solution. In non-limiting embodiments or aspects, the rooted cuttings are placed in (immersed in or otherwise kept in constant contact with) a nutrient solution containing nutrients for at least 1 day, at least 1.5 days, or longer, at somewhat higher levels of illuminance than the rooting process (e.g., 20-40 klux, optionally 25-30 klux, all subranges therebetween inclusive). In non-limiting embodiments or aspects, the cuttings are maintained in the strip, and the strip is immersed in the nutrient solution, or, a porous material. (e.g., foam) is impregnated with nutrient solution and the strip is provided thereon or in a cut or slit therein, so that the cuttings are in constant contact with the nutrient solution. Varieties of species that may benefit from such a treatment include, but are not limited to genera such as *Lobularia, Portulaca*, and *Petunia*.

In non-limiting embodiments or aspects, at least part of the cutting, for example, the root or callus, is coated with a polymer solution or suspension to protect the cutting during shipment. Suitable coating solutions/suspensions are known to those of skill in the art, and are disclosed in, for example and without limitation, International Patent Publication No. WO 2016/189021, the contents of which are incorporated herein by reference in their entirety. Suitable coatings may contain one or more polymers such as, without limitation, sodium alginate, agar, polyacrylamide, agarose, biodegradable plastics, and gelatin. In non-limiting embodiments or aspects, the solution or suspension includes one or more nutrients, growth promoters, microbial control agents, pest and/or disease control agents, antibiotics, and/or growth regulators.

While it is believed that any variety of plant will benefit from the systems and methods described herein, the following families, genera, and species are particularly suitable to propagation and rooting using the systems and methods described herein:

TABLE 1

| Family | Genus |
| --- | --- |
| Acanthaceae | *Strobilanthes* spp., *Crossandra* spp., *Rueilia* spp. |
| Aizoaceae | *Delosperma* spp., *Lampranthus* spp. |
| Amaranthaceae | *Gomphrena* spp., *Alternathera* spp., *Celosia* spp., *Iresine* spp. |
| Apocynaceae | *Hoya* spp., *Vinca* spp., *Mandevilla* spp. |
| Araceae | *Anthurium* spp. |
| Araliaceae | *Hedera* spp. |

TABLE 1-continued

| Family | Genus |
|---|---|
| Asphodelaceae | *Haworthia* spp., *Gasteria* spp., *Aloe* spp., *Astroloba* spp. |
| Asteraceae | *Achillea* spp., *Arctotis* spp., *Artemisia* spp., *Aster* spp., *Asteriscus* spp., *Brachyscome* spp., *Bidens* spp., *Boltonia* spp., *Calendula* spp., *Calocephalus* spp., *Chrysanthemum* spp., *Eupatorium* spp., *Euryops* spp., *Solidago* spp., *Osteospermum* spp., *Dahlia* spp., *Echinacea* spp., *Gerbera* spp., *Helenium* spp., *Sanvitalia* spp., *Calocephalus* spp., *Argyranthemum* spp., *Coreopsis* spp., *Helichrysum* spp., *Gaillardia* spp., *Leucanthemum* spp., *Doronicum* spp., *Senetio* spp., *Stevia* spp., *Santolina* spp., *Zinnia* spp. |
| Balsaminaceae | *Impatiens* spp. |
| Begoniaceae | *Begonia* spp. |
| Boraginaceae | *Lithodora* spp., *Heliotropium* spp. |
| Brassicaceae | *Alyssum* spp., *Lobularia* spp., *Erysimum* spp., *Iberis* spp., *Aubretia* spp. |
| Buxaceae | *Pachysandra* spp. |
| Campanulaceae | *Lobelia* spp., *Campanula* spp., *Isotoma* spp. |
| Cannaceae | *Canna* spp. |
| Caprifoliaceae | *Scabiosa* sp. |
| Caryophyllaceae | *Dianthus* spp., *Silene* spp., *Gypsophila* spp. |
| Convulvulaceae | *Ipomoea* spp., *Evolvulus* spp. |
| Crassulaceae | *Kalanchoe* spp., *Crassula* spp., *Echeveria* spp., *Graptopetalum* spp., *Sedum* spp., *Pachyveria* spp., *Sempervivum* spp., *Adromischus* spp. |
| Ericaceae | *Gaultheria* spp. |
| Euphorbiaceae | *Euphorbia* spp., *Chamaesyce* spp., *Acalypha* spp. |
| Fabaceae | *Lupinus* spp. |
| Geraniaceae | *Erodium* spp., *Geranium* spp., *Pelargonium* spp., *Saintpaulia* spp. |
| Gesneriaceae | *Streptocarpus* spp. |
| Goodeniaceae | *Scaevola* spp. |
| Hypericaceae | *Hypericum* spp. |
| Lamiaceae | *Agastache* spp., *Glechoma* spp., *Solenostemon* spp., *Ajuga* spp., *Salvia* spp., *Rosmarinus* spp., *Plectranthus* spp., *Perovskia* spp., *Lavandula* spp., *Lamium* spp., *Mentha* spp., *Monarda* spp., *Nepeta* spp., *Ocimum* spp., *Origanum* spp., *Stachys* spp., *Thymus* spp., *Perilla* spp. |
| Linderniaceae | *Torenia* spp. |
| Lythraceae | *Cuphea* spp. |
| Malvaceae | *Abutilon* spp., *Hibiscus* spp. |
| Nyctaginaceae | *Bougainvillea* spp. |
| Onagraceae | *Fuchsia* spp., *Gaura* spp., *Oenothera* spp. |
| Orchidaceae | *Phalaenopsis* spp. |
| Paeoniaceae | *Paeonia* spp. |
| Papaveraceae | *Papaver* spp. |
| Piperaceae | *Peperomia* spp. |
| Plantaginaceae | *Antirrhinum* spp., *Chelone* spp., *Veronica* ssp., *Penstemon* spp., *Digitalis* spp., *Angelonia* spp., *Lophospermum* spp. |
| Plumbaginaceae | *Limonium* spp., *Armeria* spp., *Plumbago* spp., *Ceratostigma* spp. |
| Polemoniaceae | *Phlox* spp., *Polemonium* spp. |
| Portulacaceae | *Portulaca* spp. |
| Primulaceae | *Lysimachia* spp. |
| Ranunculaceae | *Helleboris* sp., *Delphinium* spp. |
| Rosaceae | *Rosa* spp., *Geum* spp., *Waldsteinia* spp. |
| Rubiaceae | *Pentas* sp., *Galium* spp. |
| Saxifragaceae | *Heuchera* spp., *Heucherella* spp., *Saxifraga* spp., *Tiarella* spp. |
| Scrophulariaceae | *Sutera* spp., *Nemesia* spp., *Diascia* spp. |
| Solanaceae | *Petunia* spp., *Calibrachoa* spp. |
| Verbenaceae | *Aloysia* spp., *Lantana* spp., *Verbena* spp., *Duranta* spp. |
| Violaceae | *Viola* spp. |

Figure 6:
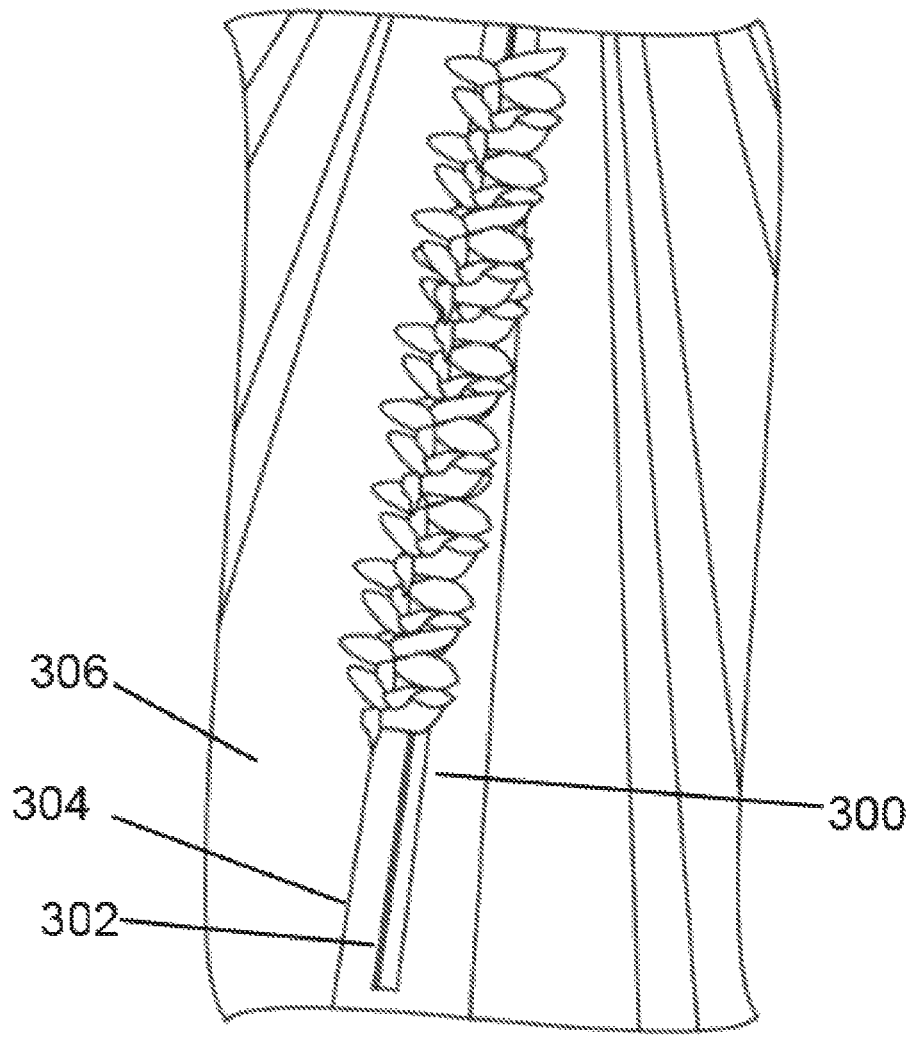
FIG. 6 is a perspective view of a non-limiting embodiment or aspect of the present invention.

In some non-limiting embodiments or aspects of the present method, the receptacle or strip of receptacles is held in a container that holds standing water or allows a flow of water or other source of humidity therethrough. The water can be provided by any means, for example, by watering the unrooted cuttings from above or by introducing water directly to the container, though, as noted previously, the water in the container does not directly contact the basal portion of the cutting. In some non-limiting embodiments or aspects, the container (300) may be tubular in shape, such as in the form of a pipe, as shown in FIGS. 6 and 7. The pipe can have a slit (302) or other opening in a sidewall thereof to allow for a receptacle or strip of receptacles (200) to be held in place, with the basal portion of the one or more unrooted cuttings being held in an interior of the pipe. The container (300) can be received and held in an opening of a support structure (306), which may be a table, platform, or other substantially horizontal surface in which openings (304) are defined and are sized for retaining one or more containers (300) by friction fit or support mechanisms (not shown). The receptacle or strip of receptacles (200) is configured or mounted within container (300) such that the basal portion of the one or more unrooted cuttings, and, eventually, calluses or roots, do not contact any standing water or water flowing through the pipe. Those of skill in the art will appreciate that the container (300) need not be tubular in shape, and that any structure or device configurable to hold unrooted cuttings, and, eventually, cuttings with calluses or roots, in a manner that allows proximity of the calluses or roots to, but not in contact with, a source of water or humidity, can be utilized in the method described herein.

As noted above with regard to other embodiments/aspects, the receptacle or strip of receptacles (200) can be supported in the container (300) in a manner that allows the basal portion of the unrooted cutting to be kept in relative darkness in the interior of the device, keeping light (natural or artificial) from above from penetrating to the basal portion of the unrooted cutting, while allowing humidification in the interior. In some non-limiting embodiments or aspects, the strip is held in the container (300) in a manner that is substantially (e.g., as much as possible) airtight, such that a constant level of humidity can be maintained in the container (300) interior where the basal portion of the cutting is maintained.

Figure 9:
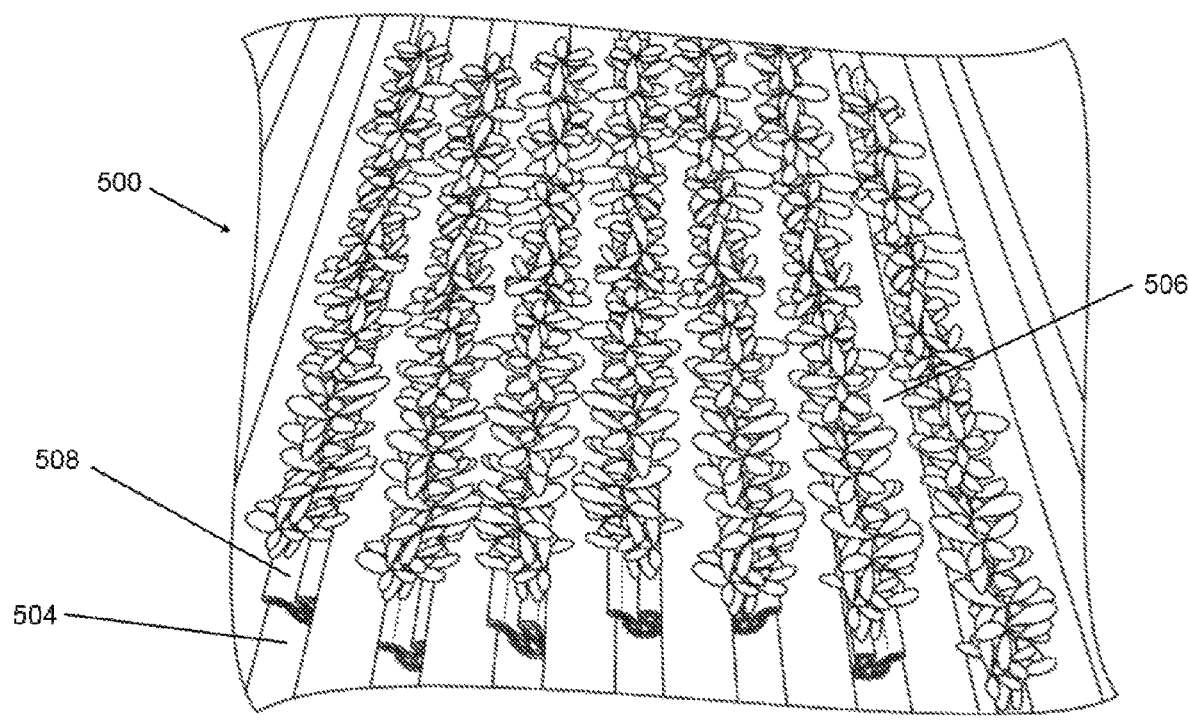
FIG. 9 is a perspective view of a non-limiting embodiment or aspect of the present invention.
Figure 10:
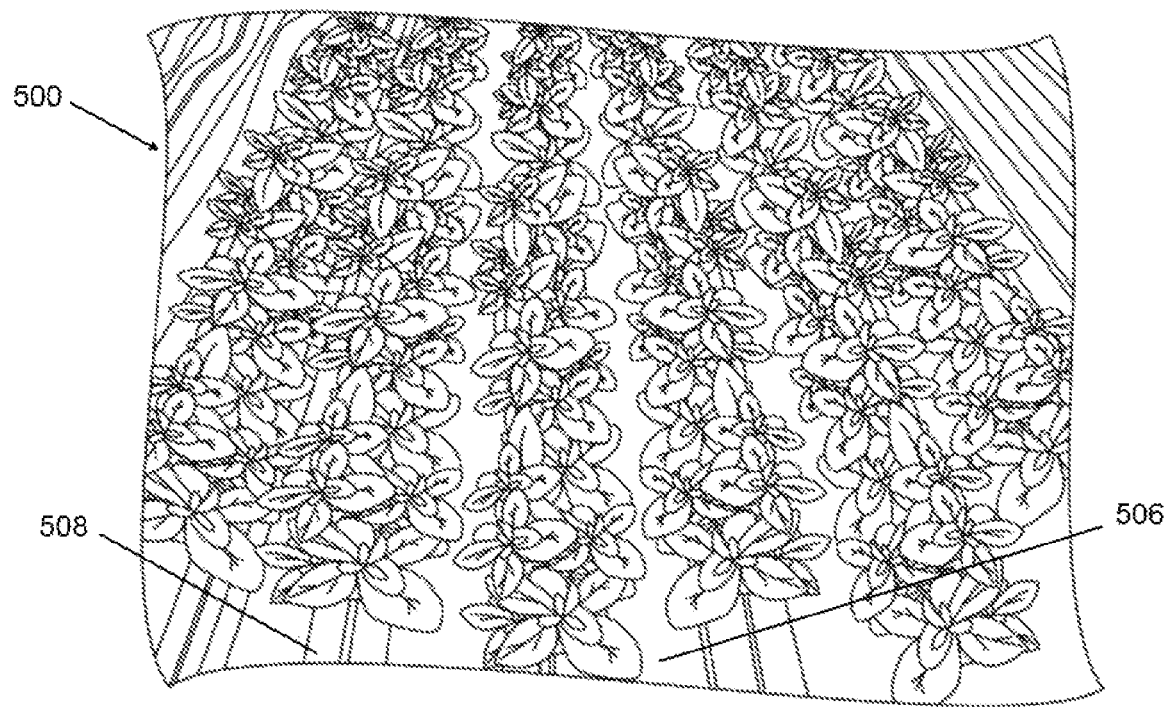
FIG. 10 is a perspective view of a non-limiting embodiment or aspect of the present invention.

The receptacle or strip of receptacles (200) can be releasably or reversibly received in the container (300) in any suitable manner, for example and without limitation by friction fit, press fit, interference fit, snap fit, by sliding the receptacle or strip of receptacles into an opening in container (300), or the like, so long as the basal portion of the unrooted cutting held in the receptacle is shielded from substantially all ambient light (for example, and without limitation, by container (300)) and is capable of being exposed to a humid environment. For example, and without limitation, receptacle or strip of receptacles (200) may include a shoulder that interacts with and rests on an upper surface of container (300), allowing the basal portion of the unrooted cutting to reside in the interior of container (300) in relative darkness. In non-limiting embodiments or aspects (for example, as shown in FIGS. 9 and 10), a material, such as a plastic film, textile, Agrivelo, and/or groundcover material, can be supplied between the receptacles and the walls of the container (300), to reduce the diameter/width of opening and allow receptacles to more snugly be held in the container (300).

In other non-limiting embodiments or aspects, the receptacle or strip of receptacles holding cuttings can be held in an opening of a support structure. Any support structure that can securely hold a strip of cuttings in an environment where the cuttings can be exposed to humidity may be useful for the method. In non-limiting embodiments or aspects, the support structure is a solid structure, such as a Styrofoam block, into which channels/gutters can be introduced. In non-limiting embodiments the support structure is a table or other flat surface having slits or grooves for holding a strip of receptacles. In non-limiting embodiments or aspects, the table or other flat surface holds the strip of receptacles over a surface that can hold or otherwise retain water, such as channels or gutters. In non-limiting embodiments or aspects the gutters or channels can be used to hold standing water to maintain humidity or to catch and retain water from overhead misting/watering, or, a flow of water can be provided through the channels or gutters.

Figure 8:
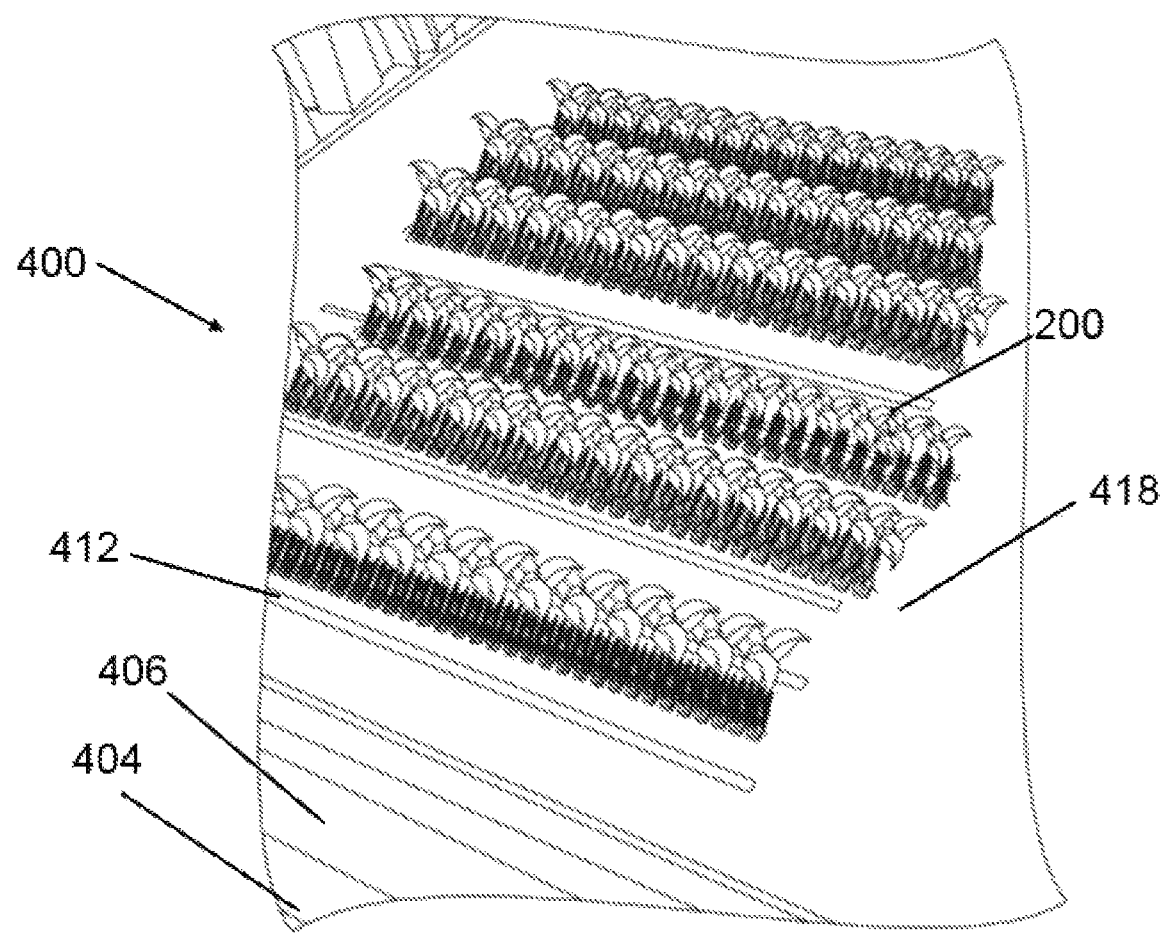
FIG. 8 is a perspective view of a non-limiting embodiment or aspect of the present invention.

Turning to FIG. 8, in some non-limiting embodiments or aspects, the receptacle or strip of receptacles (200) is held in an opening of a support structure (400) having therein a gutter or channel (404) with one or more structures (406) separating the gutters or channels (404) for the collection and/or maintenance of water or other liquid as a source of humidity. The support structure (400) can be a table or other substantially horizontal structure, having therein one or more slits (412). Water can be provided to the gutter or channel (404) by any known means. In certain non-limiting embodiments or aspects, simple watering, for example, by means of commercially-available watering or misting systems, provides water to the portion of the unrooted cutting that is held above the support structure. The slits (412) allow water to fall to the gutter or channel (404) thereunder for collection to maintain humidity for the basal portion of the unrooted cutting. In certain non-limiting embodiments or aspects, the support structure (400) is a table holding one or more gutters or channels (404). The support structure (400) can further include a covering (418), for example, a plastic or rigid material, that can hold a receptacle or strip of receptacles (200) in a position such that the basal portion of any unrooted cutting(s) held therein does not contact water held in the gutter or channel (404). In non-limiting embodiments or aspects, the covering (418) is of a dark or opaque material to maintain sufficient darkness for development of the basal portion of the unrooted cuttings, as described previously.

As noted above with regard to other embodiments or aspects, the receptacle or strip of receptacles (200) can be supported in the support structure (400) in a manner that allows the basal portion of the unrooted cutting to be kept in relative darkness in the interior of the device (e.g., 10.8 lux or lower), keeping light (natural or artificial) from above from penetrating to the basal portion of the unrooted cutting, while allowing humidification in the interior. The receptacle or strip of receptacles (200) can be reversibly or releasably received in the support structure (400) in any suitable manner, for example and without limitation by friction fit, press fit, interference fit, snap fit, by sliding the receptacle or strip of receptacles into slit (412), or the like, so long as the basal portion of the unrooted cutting held in the receptacle is shielded from substantially all ambient light (for example, and without limitation, by support structure (400)) and is capable of being exposed to a humid environment. For example, and without limitation, receptacle or strip of receptacles (200) may include a shoulder that interacts with and rests on support structure (400), allowing the basal portion of the unrooted cutting to pass through slit (412), thus residing below support structure (400) and in relative darkness.

With reference to FIGS. 9 and 10, shown are support structures (500) for receiving one or more strips (200) including receptacles, as described previously, for holding unrooted cuttings therein. As described previously, support structure can include one or more gutters or channels (504) separated by one or more separators (506). Water can be held in the gutters or channels or flow therethrough, providing humidity to the basal portion of the cutting. In the embodiments illustrated in FIGS. 9 and 10, the gutters (504) are too wide for the strips (200), thus a support material (508) is provided. As described previously, the support material can be a plastic film or the like. Those of skill in the art will appreciate that any material that can be used to narrow the uppermost portion of the gutters (504) to allow the strip (200) to fit snugly therein will be useful.

In some non-limiting embodiments or aspects, the method includes the steps of inserting a receptacle, or a strip of receptacles, holding at least one unrooted cutting into an elongated opening in the support structure (400), device (100) or container (300) as described herein above, humidifying the cuttings to develop roots or calluses, and removing the receptacle from the support structure or device.

In non-limiting embodiments or aspects of the method, as described above, the device, or covering, is formed of a material, or is coated with a material, that maintains the interior at below 10.8 lux. In further non-limiting embodiments or aspects, the interior, where the basal portion of the unrooted cutting is maintained, is kept at below 1.08 lux, at below 0.108 lux, or below 0.0108 lux, all subranges therebetween inclusive.

As described above, in a system useful for the present method, the humidity sensor and humidifier can be in communication with a computer, and the computer may maintain a suitable level of humidity within the device to allow root or callus formation.

EXAMPLES

Example 1—Cut *Chrysanthemum*

Material and Method.

Rooting method: To root cut *Chrysanthemum*, an arrangement as shown in FIG. 1 was utilized. Briefly, plates with apertures designed for strips, were placed on top of a rooting compartment. The closure between the rooting compartment and the plate was airtight. Inside the rooting compartment a thick fleece was placed to retain water to allow high humidity levels inside the compartment. Importantly, no active introduction of water, by misting or spraying, was provided to the basal portion of the cut *Chrysanthemum*. *Chrysanthemum* cuttings were used directly after harvest or after storage at 4° C. for a maximum of 10 days. After pretreatment with a rooting powder (Chryzopon rose 0.1%), *Chrysanthemum* cuttings were placed into the receptacles of 51-receptacle strips with pointed retaining extensions. The filled strips were then placed into the appropriate apertures in the plates. Once the strips were placed in the system, a plastic tent was placed on top of the system to maintain a humid environment. The system was maintained in long day conditions (20 hours light, 4 hours darkness) at 19° C. The cuttings were irrigated twice per day for 7 to 10 days depending on the variety. *Chrysanthemum* cuttings were kept in the system until the cuttings reached the stage where the root length was approximately 1 cm. Once out of the rooting system, airborne rooted cuttings were either stuck directly into growth medium or stored for various time points, either with or without protective encapsulation (as described above).

*Chrysanthemum* airborne rooted cutting storage: Airborne rooted chrysanthemums were stored for several weeks. During the storage period, a humid cloth was placed around the receptacle of each strip to maintain constant humidity around the root system. The strips were placed into plastic bags and placed vertically into closed boxes. The airborne rooted cuttings were kept at 4° C. in the dark until sticking.

*Chrysanthemum* airborne rooted cuttings encapsulation: Unprotected roots can be more susceptible to adverse conditions. To prevent losses, roots of airborne rooted cuttings were encapsulated with a polymer of sodium alginate suspension complexed with a calcium chloride solution. Rooted *Chrysanthemum* cuttings were dipped into a sodium alginate suspension of 2% (thinner coating) to 4% (thicker coating) for a few seconds before being transferred to a solution of calcium chloride (1.1% to 5%) for several minutes (note that, alternatively, calcium chloride can be sprayed to complex the coating).

Result and Discussion

Figure 11:
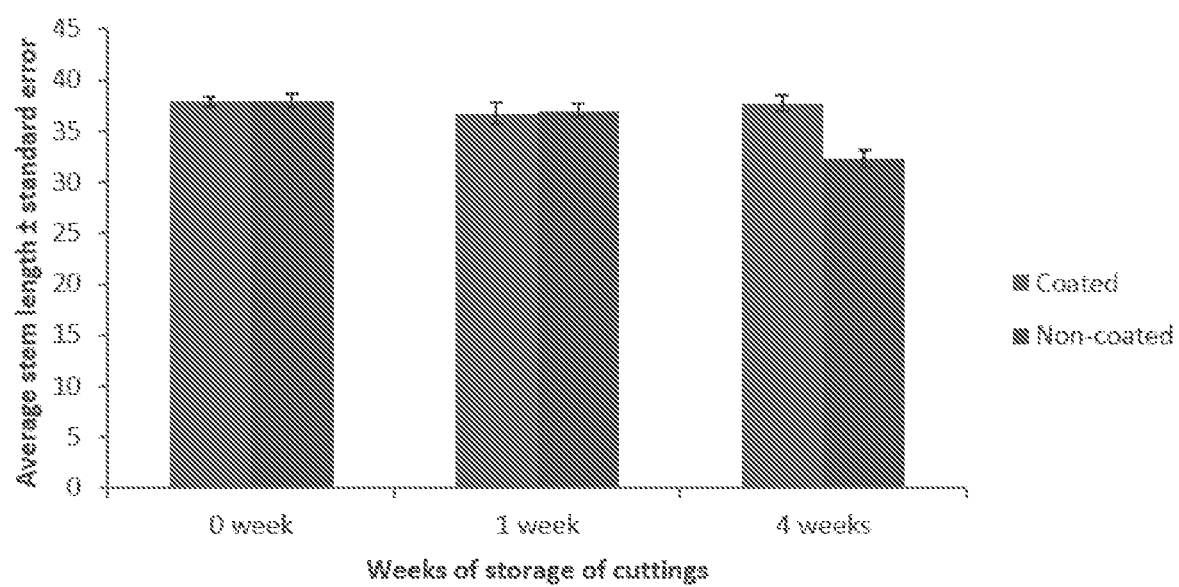
FIG. 11 is a graph showing root length of cuttings rooted according to a non-limiting embodiment or aspect of the present invention.
Figure 12:
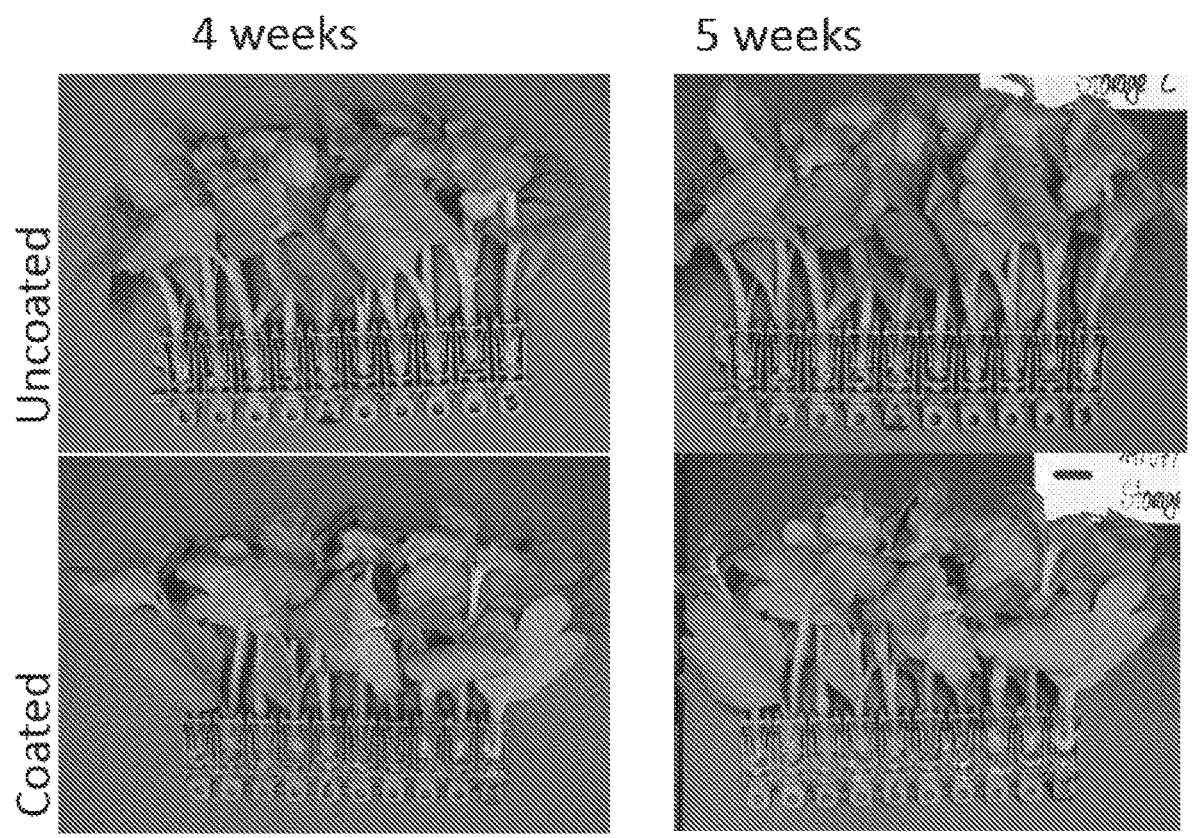
FIG. 12 is a photograph showing rooted cuttings prepared according to a non-limiting embodiment or aspect of the present invention.

To analyze the effect of airborne rooted cuttings, greenhouse performance was analyzed five weeks after transplantation in the greenhouse. The performance of airborne rooted cuttings were compared between those stored for 0, 1, and 4 weeks at 4° C., with or without encapsulation. The results are shown in FIG. 11. Interestingly, the encapsulated cuttings did not show any negative effect of the coating after 0 and 1 week of storage. Indeed the stem length of coated and un-coated *Chrysanthemum* plants were not different after 0 and 1 week of storage. However, after 4 weeks of storage, coated chrysanthemums displayed a longer stem than the uncoated samples. Additionally, the stem length of coated chrysanthemums stored for 0, 1, and 4 weeks at 4° C. was similar, suggesting a positive effect of the coating for a long term storage on the stem growth. Additionally, the coating of the cutting of chrysanthemums ensures a better quality of the product after storage (FIG. 12). After 4-5 weeks in storage, coated rooted cuttings appear fresher with a robust stem, no strong leaf discoloration, or brown roots.

The results strongly support the positive effect of the coating on stored airborne rooted cuttings. Interestingly the choice of Sodium alginate is very broad from low to high viscosity. For the encapsulation of the *Chrysanthemum* root systems, a range of viscosity between 300 to 2100 mPa·s$^{-1}$ at 20° C. allowed a good protection of the airborne rooted cuttings during the storage. Additionally the encapsulation solution can be supplemented with PGR, fertilizer, beneficials, fungicides, antiobiotics, and/or protectants to enhance the storability, protection, and greenhouse performance. Preliminary results suggest the positive effect of fertilizer in the coating.

Example 2

Styrofoam plates in which small and deep gutters were formed were used at a production farm in El Salvador. 51-receptacle strips were utilized. The strips had two types of retaining extensions: pointed and rounded. Strips with pointed retaining extensions were generally used for species of the vast majority of genera tested (e.g. *Bacopa, Bidens, Coleus, Impatiens, Lobularia, Lobelia, Chamaesyce, Scaevola, Lysimachia, Portulaca, Calibrachoa, Verbena*), and strips with rounded retaining extensions were used for *Petunia*, as the stems of *Petunia* cuttings are considerably softer. The width of the gutters was similar to the width of the strips. Friction fit maintained the strips in place and well above the bottom of the gutters in which water was retained, which created a sufficiently humid environment to support root development, but also avoided any contact of the basal portion of the unrooted cuttings with water.

In addition, *Petunia* were also kept on tables with gutters with standing water.

Two approaches were taken. First, gutters were covered with a surface in which slits were made that are sufficiently wide and long to hold the strips. The bottom of the strips was not touching the water that remained in the gutters. The humidity in the partially closed 'chamber' consisting of the gutter with the surfaces holding the strips was nearing 100%. Second, gutters which were too wide to hold the strips with the cuttings in an upright position were lined with material to reduce width (e.g. a non-porous plastic film or foam).

Plant cuttings were harvested, placed in strips, and taken to a cold room (12° C.) for two nights. Prior to rooting, the strips with the cuttings were dipped in a 300-2000 ppm solution of indole-3-butyric acid (IBA) (concentration used was species dependent). The IBA-treated strips with cuttings were placed in the gutters of the styrofoam tables. Rooting of cuttings was performed in a plastic greenhouse structure at 25-30° C. and 20-25 klux (surface illuminance, note basal portions of the unrooted cuttings were not exposed to this level of illuminance) during the day, and 15-18° C. at night at a relative humidity of 40-50% (daytime) to 100% (night). During the day the cuttings were watered overhead 5-7 times/day with a nutrient solution. In particular, during the first days of rooting, cuttings were covered with lightweight horticultural fleece or plastic to retain high humidity. From some crop species like *Bacopa, Verbena, Calibrachoa, Portulaca, Lobelia, Lobularia* and *Lysimachia*, the apical meristems were removed during rooting (pinched).

All species tested developed roots up to 2.0 cm after 8-17 days, as shown below in Table 2.

TABLE 2

| Crop Genus | Time (days) to develop ~2.0 cm roots through airborne rooting | |
|---|---|---|
| | Average | Standard Deviation |
| Bacopa | 9.7 | 1.2 |
| Bidens | 11.9 | 1.3 |
| Calibrachoa | 12 | 2.1 |
| Chamaesyce | 9.5 | 0.6 |
| Coleus | 10.2 | 0.6 |
| Dahlia | 10.5 | 1.2 |
| Lobelia | 10.8 | 1.7 |
| Lobularia | 13.1 | 2.1 |
| Lysimachia | 9 | 0 |
| NGI | 10.6 | 1 |
| Osteospermum | 15.5 | 2.2 |
| Portulaca | 9 | 0 |
| Scaevola | 17 | 0 |
| Verbena | 9 | 0.2 |
| Coreopsis | 17.7 | 4.0 |
| Euphorbia | 22.0 | 1.2 |
| Gaillardia | 15.6 | 1.8 |
| Gaura | 11.0 | 0.0 |
| Iberis | 29.8 | 2.5 |
| Lavandula | 16.8 | 2.0 |
| Phlox | 23.0 | 4.1 |
| Salvia | 16.2 | 3.2 |
| Viola | 20.7 | 1.8 |

For *Petunia* the root development was independent of the rooting setting and on average it took 13.4 days with a standard deviation of 1.1 days to develop roots of 2.0 cm in length. Certain plant species (e.g. *Lobularia, Portulaca, Petunia*) received a post-rooting nutrient treatment prior to rooting gel application, storage, or shipping.

Interestingly, plant species belonging to the genera *Lantana, Osteospermum, Euphorbia, Mandavilla, Chamaecyse*, and *Scaevola* are generally considered recalcitrant to rooting in a current commercial rooting processes involving liners, peat blocks and other rooting matrices, but, as shown above, were able to successfully be rooted in under three weeks with the present methods.

In addition, perennial varieties that were propagated through airborne rooting developed roots, though, as can be appreciated from Table 2, development of roots took somewhat longer than for annual varieties.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for airborne rooting and/or callusing of cuttings, comprising:
    placing at least one unrooted cutting having a basal portion and a top portion into at least one receptacle, wherein said basal portion is held in the receptacle, wherein the basal portion of the cutting is not in direct contact with growth medium, and liquid is not applied directly to the basal portion of the cutting; and
    humidifying the unrooted cutting to generate at least one callused or rooted cutting.

2. The method of claim 1, wherein the basal portion of the at least one unrooted cutting is kept at or below 10.8 lux.

* * * * *